219-121
6/17/80    XR    4,207,874    SR

United States Patent [19]
Choy

[11]    4,207,874
[45]    Jun. 17, 1980

[54] LASER TUNNELLING DEVICE

[76] Inventor: Daniel S. J. Choy, 892 Riverbank Rd., Stamford, Conn. 06903

[21] Appl. No.: 890,353

[22] Filed: Mar. 27, 1978

[51] Int. Cl.² ........................... A61B 1/06; B23K 9/00
[52] U.S. Cl. ..................................... 128/6; 128/303.1; 128/276; 15/300 R; 219/121 LM
[58] Field of Search ........................ 350/96.26, 96.24; 128/305, 395–397, 276, 4, 5, 6, 7, 8, 303.1, 304, 311, 328, 348, 356, 2 A, 2 M, 2 V; 219/121 L, 121 LM

[56]    References Cited
U.S. PATENT DOCUMENTS

| | | | |
|---|---|---|---|
| 3,051,176 | 8/1962 | Alberti | 128/276 |
| 3,071,129 | 1/1963 | Wasserman | 128/6 |
| 3,315,680 | 4/1967 | Silbertrust et al. | 128/395 |
| 3,565,062 | 2/1971 | Kuris | 128/24 A |
| 3,635,223 | 1/1972 | Klieman | 128/348 |
| 3,821,510 | 6/1974 | Muncheryan | 128/303.1 |
| 3,830,225 | 8/1974 | Shinnick | 128/4 |
| 3,888,239 | 6/1975 | Rubinstein | 128/2 A |
| 4,027,137 | 5/1977 | Liedtke | 128/121 L |
| 4,122,853 | 10/1978 | Smith | 128/303.1 |
| 4,146,019 | 3/1979 | Bass et al. | 128/276 |

FOREIGN PATENT DOCUMENTS

| | | | |
|---|---|---|---|
| 2640406 | 3/1978 | Fed. Rep. of Germany | 128/6 |
| 964567 | 7/1964 | United Kingdom | 128/6 |

OTHER PUBLICATIONS

*Pathology*, by Anderson, eighth edition, G. V. Mosby Co., 1972, pp. 369–374 and 415–417.

*Primary Examiner*—Robert W. Michell
*Assistant Examiner*—Arthur S. Rose
*Attorney, Agent, or Firm*—Wolder, Gross & Yavner

[57]    ABSTRACT

A device for use primarily in medical applications to locate, analyze, illuminate and destroy obstructions in a tube. The device includes a fiberoptics bundle for insertion to the tube in a flexible conduit. The conduit includes a connection to a suction source at one of its ends, a valved means of controlling the application of suction, which functions also to control the injection of locating material, and a connection to the fiberoptics bundle. The fiberoptics bundle is divided into an illuminating source bundle portion, a viewing bundle portion and a laser bundle portion. The device functions to remove obstructions in tube structures, both biological and non-biological, by insertion of the conduit sheathed device into the tube structure, distal to the obstruction. A dye, or the like, is injected and the site of the obstruction thereby determined under the guidance of image-intensified fluoroscopy. The conduit is moved toward the obstruction until resistance is felt, and the negative pressure source or suction applied to attach the conduit to the obstruction. The physical contact between the device and the obstruction, as well as the physical appearance of the obstruction, are determined by direct viewing. The obstruction is then vaporized by the laser beam with vaporized debris being constantly removed by the suction, and at the same time, the conduit is advanced by the suction, so that it is in continuous contact with the obstruction. A transparent reservoir is connected to the conduit so that upon complete tunnelling an indication thereof may be observed in the transparent reservoir.

2 Claims, 4 Drawing Figures

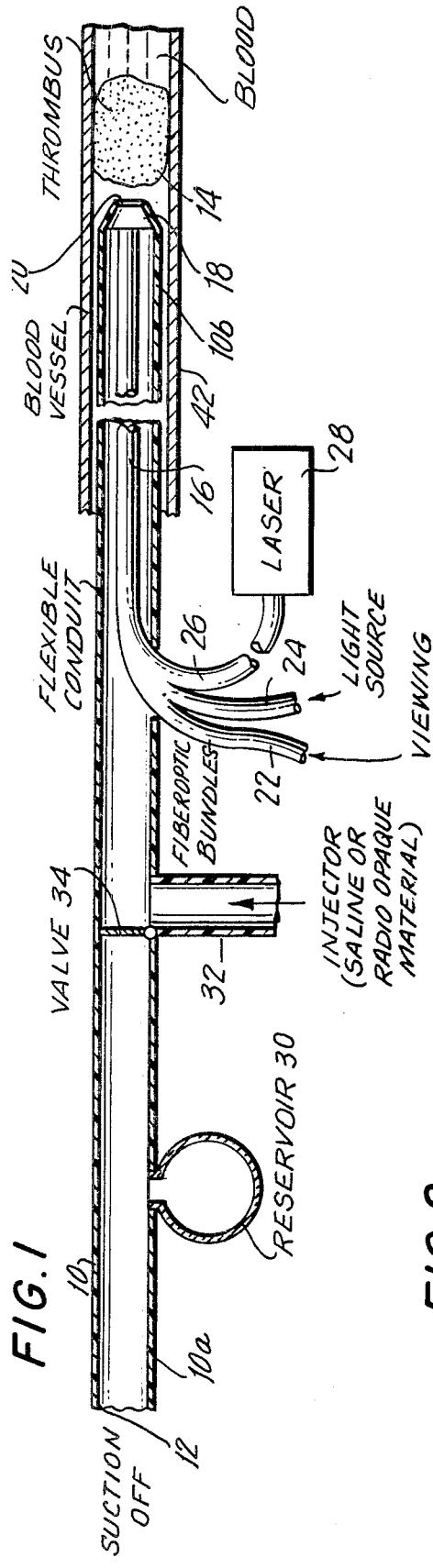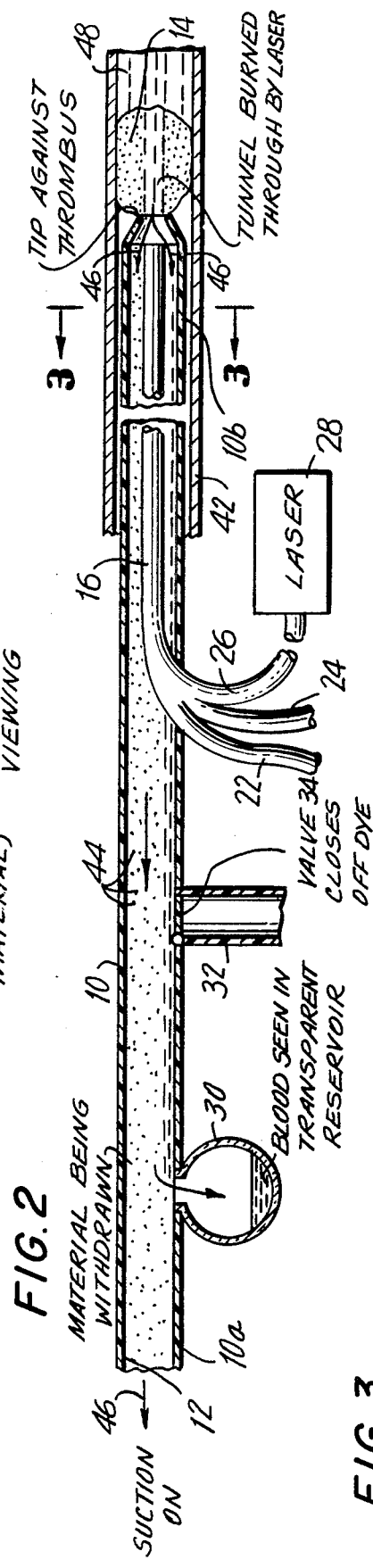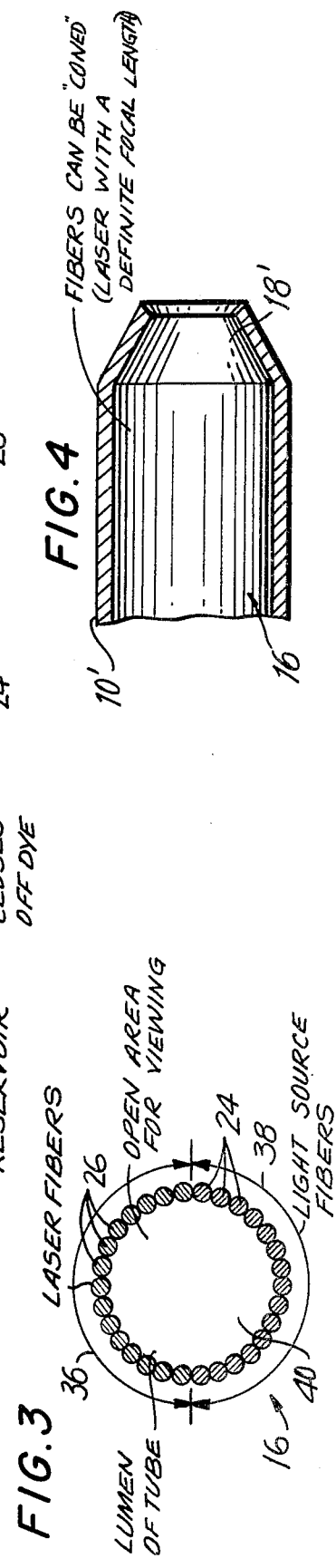

LASER TUNNELLING DEVICE

This invention relates primarily to tunnelling devices and more particularly to such devices which make use of laser and fiberoptic techniques.

For more than fifteen years now, various applications have been found for devices which are in the classification designated by the acronym "laser", indicating light amplification by the stimulated emission of radiation. Briefly, the laser device operates by using an intense source to cause ions to become inverted with respect to their normal energy distribution. The tendency of such ions is to relax to a so-called "ground state" (a normal distribution), and in so doing to stimulate inversion of other ions within the same wave length. Very promptly a laser output is achieved wherein the ion relaxation from an inverted energy state is in unison causing a massive output of energy within the wave length designated by the energy level from which the ions relax and the ground state energy level. Such energy has been used in medical applications for cauterizing, for attaching detached retinas, for removing various skin cancers and other medical applications. In industry, the laser has been used for welding and for various destructive applications as well as for other purposes. All in all, the laser has become a useful tool and promises to become a critical tool with respect to its multi-fold applications.

Likewise, for the past twenty-five or more years, fiberoptic devices have made their way in both industry and medicine. A fiberoptic device is comprised of a plurality of usually clad plastic or glass tubes wherein the cladding is of a lower index than the core for each tube. The outstanding feature of fiberoptic devices is the ability to bend light around corners. Various fiberscopes have been developed for medical technology in order to enable illuminating and viewing access by the medical practitioner to the various interior parts of the body. In many medical applications, the fiberoptic devices have been combined with the laser techniques in order to properly focus and apply the laser energy to interior parts of the body. Likewise, more mundane applications of fiberoptic techniques have been applied in industry, such as to illuminate an automobile dashboard when brake lights are on by conducting the light from the brake light substantially the length of the automobile to the indicator position.

The above cursory review of the laser and fiberoptic art indicates that the uses thereof and the combinations thereof are not new generally. U.S. Pat. No. 3,315,680 is typical, but discloses an entirely different device construction when compared to the purposes and construction of the present invention. Briefly, that patent disclosed a cauterizer using fiberoptic techniques to conduct ordinary and laser light in a medical application.

Likewise, U.S. Pat. No. 3,821,510 shows the use of a laser system which accommodates fluid flow to control the temperature of the work area. Again, this construction is vastly different when compared to the purposes and construction of the present invention. Both of the above patents are attached.

In greater detail, the present invention recognizes the functions and construction necessary to safely remove an obstruction in either a biological or non-biological application. For instance, access must be gained to the obstruction, and the device moved to close proximity therewith. Furthermore, the obstruction must be precisely located and illuminated, and in medical applications as well as industrial, fluoroscoped to guide the operation. Particularly in medical applications, the device must be flexible enough to avoid damage to the tube in which obstruction exists. The obstruction must then be destroyed and removed in a manner so as not to produce a further obstruction at another point in the tube. Finally, means must be provided to indicate the destruction and removal of the obstruction and to control the various functions of the device.

Accordingly, a primary object of the present invention is to combine the laser and fiberoptic techniques into a device whose construction enables the various functions necessary to location of, observation of, removal of and indicating removal of tube obstructions.

A further and more particular object is to provide a device of the type described which is safe, efficient and yet simple in its operation.

A still further object of the present invention is to provide a combination laser and fiberoptic device for removal of tube obstructions, which is compact in its construction.

These and other objects of the present invention are accomplished in a device according to the present invention which features a flexible conduit including connections to a fiberoptic bundle, an indicator substance for aiding in the location of the obstruction, a suction source for aiding in locating and removing the obstruction and a transparent reservoir for indicating completion of removal of the obstruction. The suction source is arranged to communicate with the device at the proximal end of an elongated, flexible conduit. At the distal end of the conduit or sheath, one end of the fiberoptic bundle is connected, with the other end dividing into viewing, light source and laser bundle portions, with appropriate sources therefor. Intermediate the distal and proximal ends of the conduit are located the transparent reservoir for indicating completion of an operation and a valved connection to an indicator substance for insertion to the conduit, used in order to enable use of fluoroscopy for location of the obstruction. The valve for the indicator substance functions both to close off insertion of the indicator substance when the removal operation begins and to close off the suction application during location operations and before removal operations. When the valve closes insertion of the indicator substance, it opens the suction to apply during the removal operation to cause debris to be conducted from the obstruction harmlessly into the suction source at the proximal end of the device.

A typical operation begins by insertion of the device of the present invention into an obstructed tube at a point distal or proximal to the obstruction. In the case of a thrombosis of a peripheral vein, the device is inserted proximal to the obstruction in the vein and the light source bundle portion activated by turning on an appropriate light source. The valve is then turned to a position to close off the suction source and to enable insertion of a saline or radio-opaque material to determine the obstruction site by the user observing a fluoroscope of the inner vein, whose character is closely indicated by use of the opaque material. The fluoroscopy is accomplished by standard equipment presently available in the art. The conduit is then advanced to the obstruction and visualized more precisely by the fluoroscope. The valve is then operated to close off the indicator substance (opaque material) and to apply the suction or negative pressure source. The suction serves to remove the opaque material and to attach the distal end of the conduit firmly to the obstruction. Further visualization is accomplished by injecting saline and direct inspection via the viewing bundle portion while the saline expands the obstructed vein. The saline is then removed by the suction. The laser beam is then activated through the laser bundle portion of the fiberoptic bundle. The laser energy vaporizes the obstruction, which is constantly removed by the suction, which also serves to advance the conduit so that it remains in contact with the obstruction. When the obstruction is tunnelled through, blood will appear in the transparent reservoir which is attached near the suction connection. The device is then withdrawn. Likewise, if the problem concerns a ureter stone, the end point of the operation will be indicated by the appearance of urine in the reservoir. Also, in the case of a common bile duct stone, the end point will be indicated by appearance of bile in the reservoir. With respect to certain industrial applications, when an airway is obstructed by a foreign body, the end point will be indicated by the appearance of air.

Other objects, features and advantages of the present invention will become more apparent by the following more detailed description of a preferred, but nonetheless illustrative, embodiment, when taken in conjunction with the attached drawings, wherein:

FIG. 1 is a schematic, side, sectional view of a device, according to the present invention, showing particularly the initial indicator operation to locate a tube obstruction and with the valve shutting off the suction source and enabling insertion to the conduit of an indicator substance;

FIG. 2 is a view similar to that of FIG. 1, but showing the device at the end of the removal operation with the indicator material shut off by the valve and the suction operating to remove the obstruction debris and with an end of the operation being indicated in the transparent reservoir;

FIG. 3 is a schematic, sectional view of the fiberoptic bundle taken along the line 3—3 of FIG. 2 and showing particularly a central lumen area surrounded by a laser bundle portion and a light source bundle portion; and FIG. 4 is a side, sectional view showing an alternative embodiment of the distal end of the fiberoptic bundle, wherein that end is coned in order to enable more precise laser focusing and application for certain obstruction problems.

Referring to the drawings, a flexible conduit 10 having proximal end 10a and proximate end 10b is provided at its proximal end with a suction opening 12. The suction opening 12 is provided to connect with a suction or negative pressure source (not shown) in order to enable precise location of conduit 10 with respect to obstruction 14 and to enable removal thereof with the present invention device. At the distal end of conduit 10 a fiberoptic bundle 16 is arranged so that it connects to a head 18 of the conduit which defines a fiber opening 20. The bundle 16 is separated from the walls of the conduit 10 by an annular space provided by means well known in the art. Fiberoptic bundle 16 includes a viewing bundle portion 22, a light source bundle portion 24 and a laser bundle portion 26, which respectively connect to an eyepiece apparatus, a light source apparatus (neither shown) and a laser apparatus 28. Laser bundle portion 26 can also serve the illumination function when the laser is operated at low intensity thereby eliminating the need for light source portion 24.

Near the proximal end of conduit 10 is arranged a transparent reservoir 30 to indicate an end to removal operations for obstruction 14. Intermediate the distal and proximal ends 10a, 10b of conduit 10 is located a connecting injector 32 for saline or radio-opaque material used as an indicator substance for the present invention. The source of the indicator substance (not shown) thereby provides a means by which the locating procedure for the present invention is enabled.

Controlling both the suction and the indicating substance is a valve 34 which functions to close off suction during the locating operation and to close off the indicating substance during the removal operation.

Referring to FIG. 3 particularly, an arrangement for fiberoptic bundle 16 is shown wherein a laser bundle portion 36 includes a plurality of laser energy conducting fibers 26 and a light source bundle portion 38 includes a plurality of light source conducting fibers 24. The central portion 40 of the fiberoptic bundle 16 is used for viewing the obstruction.

Furthermore, the distal end of conduit 10 can be arranged as shown in FIG. 4, wherein conduit 10' has its head 18' shaped in a cone configuration in order to provide a coned output for fiberoptic bundle 16. In this way, the laser energy can be more intensified and focused for certain applications, particularly medical, in order to prevent damage to blood vessels 42 (FIG. 1), and the like.

In order to provide a more complete description of the present invention, a series of operation and use steps will now be described, particularly with reference to FIGS. 1 and 2. Presuming a problem involving a thrombosis of a peripheral vein, conduit 10 is introduced to the vein 42 proximal of the obstruction 14. After the tube is only slightly advanced into vein 42, valve vale 34 is moved to the position shown in FIG. 1 and radio-opaque material put through injector 32. The conduit may then be advanced under image intensified X-ray fluoroscopy to a point where resistance is felt and juxtaposition of head 18 and thrombus obstruction 14 can be visualized. Valve 34 is then moved to a position as shown in FIG. 2 to close off injector 32 and open conduit 10 to its suction opening 12, thereby removing the radio-opaque material. Valve 34 is again returned to its position in FIG. 1. Saline is then injected, and the area of obstruction is inspected by viewing through fiberoptic bundle portion 22, with illumination provided by low intensity laser via fiberoptic bundle portion 26 or by a light source through portion 24. After the saline has been removed by suction, with valve 34 in its FIG. 2 position, the laser apparatus 28 is turned on so that it tunnels through thrombus obstruction 14 causing debris 44 to be moved in the direction of arrows 46 (FIG. 2) to the proximal end of conduit 10. When complete tunnelling has been achieved through obstruction 14, blood 48 on the other side of the obstruction from conduit 10 will be moved along with the debris toward suction opening 12 so that blood 48 will be seen in transparent reservoir 30. In this way an indication of the end of the operation will be readily observed by the user to prevent undesirable consequences with respect removal and/or obstruction what is beyond the obstruction 14.

Of course, the present invention has many other applications, all of which should be deemed to be within the purview of the present invention as illustrated with respect to certain different problems.

Accordingly, the invention is only to be limited by the scope of the following claims.

What is claimed is:

1. A device for locating, viewing and removing an obstruction in a tube comprising, in combination: an elongated sheath having distal and proximal ends; a head defining a head opening at said distal end; a fiber-optic bundle through a portion of said sheath, connected to said head and having a viewing bundle portion for use in viewing said obstruction, a laser bundle portion for use in removing said obstruction and a light source bundle portion usable with said viewing bundle portion for viewing said obstruction, said bundle portions terminating at said head opening and therewith defining a suction inlet; said bundle and said sheath together defining an annular space therebetween; a suction opening at said proximal end; an indicating substance connection opening to said annular space intermediate said ends for use in locating said obstruction by conducting an indicating substance to said obstruction; and, a transparent end of removal indicating reservoir proximate said proximal end.

2. The invention according to claim 1 wherein said device further includes a valve for controlling flow through said suction opening, said indicating substance connection and said annular space.

* * * * *